United States Patent

US 9,402,802 B2

(12) United States Patent
Kriwet et al.

(10) Patent No.: US 9,402,802 B2
(45) Date of Patent: Aug. 2, 2016

(54) TOPICAL COMPOSITIONS COMPRISING ASCOMYCINS

(75) Inventors: Katrin Kriwet, Grenzach-Wyhlen (DE); Dorothea Ledergerber, Lörrach (DE); Jutta Riedl, Grenzach (DE)

(73) Assignee: MEDA Pharma SARL, Luxembourg (LU)

( * ) Notice: Subject to any disclaimer, the term of this patent is extended or adjusted under 35 U.S.C. 154(b) by 202 days.

(21) Appl. No.: 13/204,489

(22) Filed: Aug. 5, 2011

(65) Prior Publication Data

US 2012/0202841 A1 Aug. 9, 2012

Related U.S. Application Data

(63) Continuation of application No. 11/266,639, filed on Nov. 3, 2005, now abandoned, which is a continuation of application No. 09/871,367, filed on May 31, 2001, now abandoned, which is a continuation of application No. PCT/EP99/09351, filed on Dec. 1, 1999.

(30) Foreign Application Priority Data

Dec. 3, 1998 (GB) .................................. 9826656.2

(51) Int. Cl.
| A61K 9/00 | (2006.01) |
| A61K 31/4353 | (2006.01) |
| A61K 31/436 | (2006.01) |
| A61K 47/02 | (2006.01) |
| A61K 47/06 | (2006.01) |
| A61K 47/10 | (2006.01) |
| A61K 47/12 | (2006.01) |
| A61K 47/14 | (2006.01) |
| A61K 47/16 | (2006.01) |
| A61K 47/44 | (2006.01) |

(52) U.S. Cl.
CPC ............. *A61K 9/0014* (2013.01); *A61K 31/436* (2013.01); *A61K 31/4353* (2013.01); *A61K 47/02* (2013.01); *A61K 47/06* (2013.01); *A61K 47/10* (2013.01); *A61K 47/12* (2013.01); *A61K 47/14* (2013.01); *A61K 47/16* (2013.01); *A61K 47/44* (2013.01)

(58) Field of Classification Search
None
See application file for complete search history.

(56) References Cited

U.S. PATENT DOCUMENTS

| 3,574,854 | A |   | 4/1971 | Bossard |  |
| 3,666,863 | A | * | 5/1972 | Swanbeck | 514/554 |
| 4,025,310 | A |   | 5/1977 | Bolz et al. |  |
| 4,309,206 | A | * | 1/1982 | Michaud et al. | 71/28 |
| 4,324,811 | A |   | 4/1982 | Eugley |  |
| 4,401,650 | A | * | 8/1983 | Salamone | 424/78.27 |
| 4,488,989 | A | * | 12/1984 | Lamberti | 510/429 |
| 4,612,331 | A |   | 9/1986 | Barratt et al. |  |
| 4,672,078 | A |   | 6/1987 | Sakai et al. |  |
| 4,690,774 | A |   | 9/1987 | Vishnupad et al. |  |
| 4,826,677 | A | * | 5/1989 | Mueller et al. | 424/78.05 |
| 4,963,555 | A |   | 10/1990 | Jones et al. |  |
| 5,002,760 | A |   | 3/1991 | Katzev |  |
| 5,143,918 | A |   | 9/1992 | Bochls et al. |  |
| 5,225,403 | A |   | 7/1993 | Treiber et al. |  |
| 5,352,671 | A |   | 10/1994 | Baumann et al. |  |
| 5,385,907 | A |   | 1/1995 | Asakura et al. |  |
| 5,385,938 | A | * | 1/1995 | Yu et al. | 514/557 |
| 5,559,098 | A |   | 9/1996 | Wohlrab et al. |  |
| 5,912,238 | A |   | 6/1999 | Baumann et al. |  |
| 5,925,649 | A |   | 7/1999 | Hersperger et al. |  |
| 5,939,427 | A | * | 8/1999 | Kagayama et al. | 514/291 |
| 5,981,464 | A |   | 11/1999 | He et al. |  |
| 6,113,892 | A |   | 9/2000 | Newell et al. |  |
| 6,124,362 | A |   | 9/2000 | Bradbury et al. |  |
| 6,322,829 | B1 |  | 11/2001 | McGlynn et al. |  |
| 6,352,998 | B2 |  | 3/2002 | Jackman et al. |  |

FOREIGN PATENT DOCUMENTS

| DE | 195 49 243 A1 | 6/1997 |
| DE | 196 06 355 A1 | 8/1997 |
| EP | 0 069 512 B1 | 6/1986 |
| EP | 0 184 162 A2 | 6/1986 |
| EP | 0 315 978 A2 | 5/1989 |
| EP | 0 323 042 A1 | 7/1989 |
| EP | 0 364 211 A1 | 4/1990 |
| EP | 0 423 714 A2 | 4/1991 |
| EP | 0 427 680 A1 | 5/1991 |
| EP | 0 465 426 A1 | 1/1992 |
| EP | 0 474 126 A1 | 3/1992 |
| EP | 0 484 936 A1 | 5/1992 |
| EP | 0 532 088 A1 | 3/1993 |
| EP | 0 532 089 A1 | 3/1993 |
| EP | 0 569 337 A1 | 11/1993 |
| EP | 0 626 385 A1 | 11/1994 |
| EP | 0 512 109 B1 | 11/1995 |
| EP | 0 780 129 A2 | 6/1997 |
| EP | 937453 A2 * | 8/1999 |
| EP | 1 074 255 A1 | 2/2001 |
| GB | 2 142 238 A | 1/1985 |

(Continued)

OTHER PUBLICATIONS

Hagermann., I. "Topical treatment by urea reduces epidermal hyperproliferation and induces differentiation in psoriasis.", Acta, Derm, Venereol., 1996, Abstract p. 1.*

(Continued)

*Primary Examiner* — Michael G Hartley
*Assistant Examiner* — Lance Rider
(74) *Attorney, Agent, or Firm* — Crowell & Moring LLP

(57) ABSTRACT

The present invention relates to a composition for topical administration comprising an ascomycin and a carrier vehicle comprising means to retain water in the outer skin layer and means to hinder water evaporating from the skin.

7 Claims, No Drawings

(56) References Cited

FOREIGN PATENT DOCUMENTS

| | | | |
|---|---|---|---|
| JP | 60-228423 A | 11/1985 | |
| JP | 62-223163 A | 10/1987 | |
| JP | 4-182429 A | 6/1992 | |
| JP | 5-25046 A | 2/1993 | |
| JP | 5-43457 A | 2/1993 | |
| JP | 7-252150 A | 10/1995 | |
| JP | 8-34731 A | 2/1996 | |
| JP | 8-133979 A | 5/1996 | |
| JP | 8-143458 A | 6/1996 | |
| JP | 8-231369 A | 9/1996 | |
| JP | 9-315954 A | 12/1997 | |
| JP | 10-231248 A | 9/1998 | |
| JP | 10-251137 A | 9/1998 | |
| WO | WO 91/13889 A1 | 9/1991 | |
| WO | WO 91/13899 A1 | 9/1991 | |
| WO | WO 91/19495 A1 | 12/1991 | |
| WO | WO 92/11860 A1 | 7/1992 | |
| WO | WO 93/05059 A1 | 3/1993 | |
| WO | WO 94/28894 A1 | 12/1994 | |
| WO | WO 95/19162 A1 | 7/1995 | |
| WO | WO 96/13249 A1 | 5/1996 | |
| WO | WO 96/13273 A1 | 5/1996 | |
| WO | WO 96/31514 A1 | 10/1996 | |
| WO | WO 96/38135 A1 | 12/1996 | |
| WO | WO 97/08182 A1 | 3/1997 | |
| WO | WO 97/23242 A1 | 7/1997 | |
| WO | WO 99/01458 A1 | 1/1999 | |
| WO | WO 99/20261 A2 | 4/1999 | |
| WO | WO 99/24036 A1 | 5/1999 | |
| WO | WO 00/01385 A1 | 1/2000 | |

OTHER PUBLICATIONS

Magdassi, et al., Novel Cosmetic Delivery Systems, Marcel Dekker, Dec. 2, 1998, pp. 80-81.*
Swanbeck, G., "Urea as a single drug in dry skin", Hautarzt, 1998, Abstract pp. 1.*
Mrowietz et al., "The novel ascomycin SDZ ASM 981 . . . ", British Journal of Dermatology, 1998, vol. 139, pp. 992-996.
Therapeutic House, Allergy Elimination Center (home page, pp. 1-3), see skin care section on p. 3, 2002.
"Aquadrate Cream", ABPI Data Sheet Compendium, Datapharm Publications, (Ed. G. Wlaker), p. 1227 (1993-1994).
"Handbook of Pharmaceutical Excipients" (Eds. A. Wade and P. J. Weller} Degussa, Germany (1994), joint publication of American Pharmaceutical Association, Washington, USA, and the Pharmaceutical Press, London, England pp. 367, 379, 424-427,473.
Aoyama et al., "Successful Treatment of Resistant Facial Lesions of Atopic Dermatitis with 0.1% FK506 Ointment", Br. J. Derm., vol. 133, pp. 492-500 (1995}.
British Nat. Formula, Br. Med. Assoc. and Royal Pharm. Soc., vol. 36, pp. 478-483, Sect. 13.2.1 (1998).
Dermatika (Eds. R. Nieder, J. Ziergenmeyer), Wissenschaftliche Verlagsgesellschaft Stuttgart, pp. 271-272 (1992).
Dumont et al., "A Tacrolimus-Related Immunosuppressant with Reduced Toxicity", Transplantation, vol. 65, No. 1, pp. 18-26 (1998).
Fartasch, "Epidermal Barrier in Disorders of the Skin", Microscopy Research and Technique, vol. 38, pp. 361-372 (1997).
Fiedler, "Lexikon der Hilfsstoffe fur Pharmazie, Kosmetik und angrenzende Gebiete", Editio Cantor Verlag Aulendorf, Aulendorf,4th revised and expanded edition, vol. 2., pp. 720, 736-738, 1013-1017, 1139-1142, 1198, 1303, 1635-1637,1651-1652, (1996).
Friend, "Transdermal Delivery of Levonorgestrel", Medicinal Research Reviews, vol. 11, No. 1, pp. 49-80 (1991).
Gelbe Liste 1998, "Indikatlonen/Substanzgruppen: Dermatologika, Topische Antipsoriatika und tihnliche Prtiparate".
Hagemann et al., "Topical Treatement by Urea Reduces Epidermal Hyperproliferation and Induces Differentiation in Psoriasis", Acta. Derm. Verereol. (Stockh), vol. 76, pp. 353-356 (1996).

Kalbitz et al., "Modulation der Wirkstoffpenetration in die Haut", Pharmazie, vol. 51, No. 9, pp. 619-637 (1996).
Loden, "Urea-Containing Moisturizers Influence Barrier Properties of Normal Skin", Arch. Dermatol. .Res., vol. 288, pp. 103-107 (1996).
Matsumoto et al., "Safety Study of AG-1 Cream", Yakuri to Chiryo, vol. 19, No. 5, pp. 1717-1726 (1991)-CA 115:142123j.
Mollison et al., "A Macrolactam Inhibitor ofT Helper Type 1 and T Helper Type 2 Cytokine biosynthesis for Topical Treatment of Inflammatory Skin Diseases", J. Inv.Derm., vol. 112, No. 5, pp. 729-738 (May 1999).
Neubert et al., "Wirkstoffpenetration in die Haut und deren Modulation", PZ, vol. 141, No. 17, pp. 11-16, 18,21-23, (1996)-[34-00937 & 1996:281550 CAPLUS].
Peterson et al., "A Tacrolimus-Related Immunosuppressant with Biochemical Properties Distinct From Those of Tacrolimus", Transplantation, vol. 65, No. 1, pp. 10-18 (1998).
Prausnitz, "Reversible Skin Permeabilization for Transdermal Delivery of Macromolecules", Criticial Review in Therapeutic Drug Carrier Systems, vol. 14, No. 4, pp. 455-483 (1997).
Rappersberger et al., "Clearing of Psoriasis by a Novel Immunosuppressive Macrolide", J. Invest. Derm., vol. 106, No. 4, pp. 701-710,(1996).
Racz et al., Wassergehalt der Epidermis nach Salizylas ure-und Harnstoffbehandlung, Hautarzt, vol. 40, pp. 61-62 (1980).
Ruzicka et al., "A Short-Term Trial ofTacrolimus Ointment for Atopic Dermatitis", N. Eng. J. Med., vol. 337, No. 12, pp. 816-821 (1997).
Schmook et al., "Penetration of Sandimmune (Cyclosporin A) in Rat Skin in vitro—Effects of Penetration Enhancers and Solvents", Skin Pharmacal, vol. 6, pp. 116-124 {1993).
Takahashi et al., "Effect of Vehicles on Diclofenac permeation across Excised Rat Skin", Bioi. Pharm. Bull., vol. 18, No. 4, pp. 571-575 (1995).
Tanuma et al., "Clinical Evaluation of Bifonazole for Moccasin-Type Tinea Pedis", Mycoses, vol. 40, pp. 223-228 (1997).
Torres-Rodriguez et al., "Non-Traumatic Topical Treatment of Onychomycosis with Urea Associated with Bifonazole", Mycoses, vol. 34, pp. 499-304 (1991).
Wohlrab, EinfOhrung Neurodermitis und Harnstoff, Hautarzt, vol. 43, pp. 1-4 (1992).
Wohlrab, "Vehikelabh ngigkeit der Harnstoffpenetration in die menschliche Haut", Dermatologica, vol. 169, pp. 53-59 (1984).
Wong et al., "Development of Some New Non-Toxic Biodegradable Dermal Penetration Enhancers", J. Pharm. Sci., vol. 76, No. 11, p. S59 (1987).
Wong et al., "Unsaturated Cyclic Ureas as New Nontoxic Biodegradable Transdermal Penetration Enhancers 1: Systhesis", J. Pharm. Sci., vol. 77, No. 11, pp. 967-971 (1988).
Wong et al., "Unsaturated Cyclic Ureas as New Non-Toxic Biodegradable Transdermal Penetration Enhancers. II. Evaluation Study", International Journal of Pharmaceutics, vol. 52, pp. 191-202 (1989).
Hatanaka et al., "FR-99520 and FR-900523, Novel Immunosuppressants Isolated From a Streptomyces II. Fermentation, Isolation and Physico-Chemical and Biological Characteristics", The Journal of Antibiotics, vol. XLI. No. 11. pp. 1592-1601 (1988).
Matsumoto et al., Pharmaceutics Manual, Nanzando, Japan, pp. 60, 101 and 102 (1989)—Abstract.
Definition "Humectant", hyperdictionary, (www.hyperdictionary.com), 2000-2003.
Registry file, Database STN/CAS, 33-epi-chloro-33-desoxyascomycin.2005.
Jacobi, Humectants versus Moisturisers, Soap, Perfumery & Cosmetics, Jan. 1972, pp. 111-112, see full text.
Kohno et al., Usefulness of Skin hydration for skin care and development of cosmetics, Database Caplus, AN2003:203848, abstract, Nippon Keshohin Gijutsusha Kaishi, 2002, vol. 36(4), pp. 253-261.

(56) References Cited

OTHER PUBLICATIONS

Henney et al., Humectant in Cosmetic emulsions, Database CAPLUS, An 1959:31011, abstract only, Journal of the society of cosmetic chemists, 1958, vol. 9, pp. 329-336.

Goh, Exogenous Dermatology, vol. 1, "The Role of Skin Moisturizers in the Prevention of Irritant Contact Dermatitis—A Review", pp. 180-185, (2002).

* cited by examiner

TOPICAL COMPOSITIONS COMPRISING ASCOMYCINS

This invention relates to topical compositions containing ascomycins for treatment of skin disorders, e.g. subacute and chronic inflammatory and hyperproliferative skin diseases, e.g. atopic dermatitis, vitiligo, psoriasis, lichenified skin diseases, e.g. lichen planus, a lichenified form of atopic dermatitis.

Ascomycins have a variety of useful pharmacological actions, e.g. immunosuppression, and which may be administered topically. However, inter alia because of their physicochemical properties, e.g. high molecular weight and lipophilicity the ascomycins have posed problems for topical administration.

Skin disorders also present difficulties in treatment, particularly lichenified skin diseases, e.g. psoriasis, where the skin is hyperproliferated and the skin barrier function and skin lipid composition may have changed. Topical compositions for use in lichenified skin diseases, e.g. psoriasis, containing an ascomycin present particular difficulties.

After exhaustive testing it has now been surprisingly found that the compositions of the present invention serve to enhance penetration of active agent through human skin, e.g. for the treatment of lichenified skin diseases, e.g. psoriasis. These compositions show other particularly interesting properties, e.g. they are easily applied to large areas of the skin and are stable.

In one aspect this invention provides a composition for topical administration of an ascomycin which composition comprises a carrier vehicle comprising
  (i) means to retain water in the outer skin layer, and
  (ii) means to hinder water evaporating from the skin.

The ascomycin is hereafter referred to as active agent. Under "ascomycin" is to be understood ascomycin itself or a derivative, antagonist, agonist or analogue thereof, e.g. a compound of the FK 506 class.

FK506 is a known macrolide antibiotic that is produced by *Streptomyces tsukubaensis* No 9993. It is also a potent immunosuppressant. The structure of FK506 is given in the appendix to the Merck Index, 11th Edition as item A5. Methods of preparing FK506 are described in EP 184162.

Under "compound of the FK 506 class" is to be understood FK 506 itself or a derivative, antagonist, agonist or analogue thereof, which retain the basic structure and modulate at least one of the biological properties (for example immunological properties) of FK506. A large number of compounds of the FK 506 class are known. These compounds are described in for example EP 184162, EP 315978, EP 323042, EP 423714, EP 427680, EP 465426, EP 474126, WO 91/13889, WO 91/19495, EP 484936, EP 532088, EP 532089, EP 569337, EP 626385, WO 93/5059 and the like.

It is also known (for example from EP 315978 and EP 474126) that ascomycin derivatives such as macrolactam compounds of the FK506 class are particularly useful in the topical treatment of inflammatory and hyperproliferative skin diseases and of cutaneous manifestations of immunologically-mediated illnesses.

Thus examples of ascomycin derivatives suitable for use in the present invention include FK506; 33-epi-chloro-33-desoxy-ascomycin as disclosed in Example 66a in EP 427 680 (hereafter referred to as Compound A);
{[1E-(1R,3R,4R)]1R,4S,5R,6S,9R,10E,13S,15S,16R,17S,19S,20S}-9-ethyl-6,16,20-trihydroxy-4-[2-(4-hydroxy-3-methoxy-cyclohexyl)-1-methylvinyl]-15,17-dimethoxy-5,11,13,19-tetramethyl-3-oxa-22-aza-tricyclo[18.6.1.0(1,22)] heptacos-10-ene-2,8,21,27-tetraone as disclosed in Examples 6d and 71 in EP 569 337 (hereafter referred to as Compound B); and
{1R,5Z9S,12S-[1E-(1R,3R,4R)],13R,14S,17R,18E,21S,23S,24R,25S,27R}17-ethyl-1,14-dihydroxy-12-[2-(4-hydroxy-3-methoxy-cyclohexyl)-1-methylvinyl]-23,25-dimethoxy-13,19,21,27-tetramethyl-11,28-dioxa-4-aza-tricyclo[22.3.1.0(4,9)]octacosa-5,18-diene-2,3,10,16-tetraone, also known as 5,6-dehydro-ascomycin as disclosed in Example 8 in EP 626 385 (hereafter referred to as Compound C);

Imidazolylmethyloxyascomycin, as disclosed in Example 1 and as compound of formula I in WO 97/08182, contents of which are incorporated herein by reference (hereafter referred to as Compound D);

32-O-(1-hydroxyethylindol-5-yl)ascomycin, also known as Indolyl-ASC or L-732 531 as disclosed in Transplantation 65 (1998) 10-18, 18-26, on page 11, FIG. 1 (hereafter referred to as Compound E); and (32-deoxy-32-epi-N1-tetrazolyl)ascomycin, also known as ABT-281 as disclosed in J. Inv. Derm. 112 (May 1999), 729-738, on page 730, FIG. 1 (hereafter referred to as Compound F).

FK 506, Compounds A, B, C, D, E, and F are preferred ascomycins, particularly preferred are Compounds A, B, and C, especially Compound A.

The active agent is e.g. present in the compositions of this invention in an amount of from 0.05 to 3% by weight, e.g. from 0.1 to 2% by weight, e.g. from 0.4 to 1% by weight based on the total weight of the composition.

The active agent may be dissolved, e.g. partially dissolved in the vehicle. In a further aspect the active agent may be in suspension, e.g. partially in suspension in the vehicle. Preferably the active agent is partially dissolved in the vehicle.

Preferably the active agent may be used in a micronized form. The suspension may contain particles of ascomycin of from 5, e.g. from 10, to about 90, preferably to about 25 microns in diameter. The particles of the ascomycin may be produced in conventional manner, e.g. by grinding or milling.

If desired further active agents may be present.

The carrier vehicle comprises means to retain water in the outer skin layer, e.g. moisturizers.

Under "means to retain water in the outer skin layer" is to be understood, e.g. a pharmaceutically acceptable moisturizer, capable of e.g. penetrating and residing in the outer skin layer, e.g. the stratum corneum, and e.g. absorbing, holding and retaining moisture to increase the moisture content of the skin.

Means to retain water in the outer skin layer, e.g. moisturizers, e.g. as described in Dermatika, Eds. R. Nieder, J. Zegenmayer, Wissenschaftliche Verlagsgesellschaft Stuttgart 1992, 271-272, may be selected from a group comprising
  i) a urea, e.g. urea and its derivatives, e.g. monoacetyl urea, 1-dodecyl urea, 1,3-didodecyl urea, 1,3 diphenyl urea or cyclic urea derivatives, e.g. 1-methyl-4-imidazolin-2-one-3-methylenedecanoate. Urea may be commercially available from e.g. Merck, Germany;
  ii) an inorganic salt, e.g. sodium chloride, e.g. as known and commercially available from e.g. Merck, Germany; and
  iii) a carboxylic acid, e.g. a mono carboxylic acid or a cyclic carboxylic acid, salts and derivatives thereof. Particularly preferred are e.g. lactic acid; glycolic acid; lactic acid sodium and/or ammonium salt, e.g. sodium lactate, e.g. as known and commercially available from e.g. Merck, Germany; glycolic acid sodium and/or ammonium salt; lactamide; lactamidopropyl-triammonium chloride; sodium cocoyl lactylate; 2-pyrrolidone-5-carboxylate; 2-pyrrolidone-5-carboxylate sodium and/or calcium salt, e.g. sodium 2-pyrrolidone-5-carboxylate, e.g. as known and commercially available under the name Sodium PCA from A+E Connock, UK; 2-pyrrolidone-5-carboxylate derivatives of amino acids, e.g. lysin or arginin; or acyl esters, having e.g. a chain length of $C_1$-$C_{30}$, e.g. $C_3$-$C_{18}$, branched or unbranched, e.g 2-pyrrolidone-5-carboxylic laurate (Fiedler, H. P. "Lexikon der Hilfsstoffe für Pharmazie, Kosmetik and angrenzende Gebiete", Editio Cantor Verlag Aulendorf, Aulendorf, 4th revised and expanded edition (1996), 1, p. 720; 2, p. 1013-1017; 2, p. 1303)

Mixtures thereof may also be used.

Preferably the carrier vehicle comprises a urea, e.g. urea itself or derivatives thereof, e.g. monoacetyl urea, 1-dodecyl urea, 1,3-didodecyl urea, 1,3 diphenyl urea or cyclic urea derivatives, e.g. 1-methyl-4-imidazolin-2-one-3-methylene-decanoate.

Particularly preferred is urea itself.

The means to retain water in the outer skin layer, e.g. urea, may be present in amount of from 0.1 to about 20%, e.g. from 1 to about 15%, preferably about 5% by weight based on the total weight of the composition. The means to retain water in the outer skin layer may be suspended or dispersed in the vehicle. They may be used in a micronized or non micronized form. Particularly preferred is the micronized form. The suspension or dispersion may contain particles of, e.g., urea of from 5, e.g. from 10, to about 90, preferably to about 25 microns in diameter. The non-micronized particles may have a size of equal to or less than 500 microns. The particles of the urea may be produced in conventional manner, e.g. by grinding or milling.

Preferably the ascomycin and the means to retain water in the outer skin layer are present in a weight ratio of 0.05 to 3:0.1 to 20, more preferably in a weight ratio of 0.1 to 2:5 to 15, even more preferably in a weight ratio of 0.4 to 1:about 5.

The carrier vehicle further comprises means to hinder water evaporating from the skin, e.g. hydrocarbons. Hydrocarbons may be selected from a group comprising
i) petrolatum, e.g. white petrolatum, e.g. as known and commercially available from e.g. Mineral Chemie AG, Germany;
ii) liquid paraffin, e.g. as known and commercially available from e.g. Mobil BP Oiltech, Switzerland;
iii) solid paraffin; or microcrystalline wax, e.g. as known and commercially available under the trade name Esma® M from Schlüter, Germany; and
iv) a reaction product of a paraffin and a polyethylene, e.g. a polyethylene having a molecular weight of from 10000 to about 400000 Daltons, e.g. 21000 Dattons, e.g. as known under the name Hydrophobes Basisgel DAC and commercially available under the trade name Plastibase®, from e.g. Hansen & Rosenthal, Germany (Fiedler, H. P., loc. cit, 2, p. 1198).

Mixtures thereof may also be used.

Hydrocarbons may be present in amount of from 70 to about 95%, preferably of from 75 to about 90%, more preferably about 85% by weight based on the total weight of the composition.

The amount and the type of hydrocarbons in the composition may depend on the desired viscosity of the composition as is conventional.

Preferably the ascomycin and the hydrocarbon are present in a weight ratio of 0.05 to 3:70 to 95, more preferably in a weight ratio of 0.1 to 2:75 to 90, even more preferably in a weight ratio of 0.4 to 1:about 85.

In another aspect the present invention provides a composition as defined above which composition comprises a carrier vehicle comprising
(i) a urea, an inorganic salt, or a carboxylic acid, and
(ii) a hydrocarbon.

Under "a carboxylic acid" is to be understood a mono carboxylic acid or a cyclic carboxylic acid, salts and derivatives thereof, e.g. as defined above. Under "a urea" is to be understood urea it self or a derivative thereof, e.g. as defined above.

In another aspect the present invention provides a composition as defined above which composition comprises a carrier vehicle further comprising
(iii) liquid means, e.g. lipophilic solvents and/or polar solvents, to solubilize ascomycin.

The lipophilic solvents may be selected from a group comprising
i) liquid waxes, e.g. natural-, synthetic-, semisynthetic- or emulsifying-waxes. Preferably isopropyl myristate, e.g. as known and commercially available from Henkel, Germany; oleyl erucate, e.g. as known and commercially available under the trade name Cetiol® J600 from e.g. Henkel, Germany; diisopropyl adipate, e.g. as known and commercially available under the trade name Isopat® 1794 from e.g. Dargoco, Germany; and/or oleyl oleate, e.g. as known and commercially available under the trade name Cetiol® from e.g. Henkel, Germany, may be used;
ii) liquid fatty alcohols, saturated and/or unsaturated, branched and/or unbranched, having e.g. a $C_8$ to $C_{24}$ chain. Preferably oleyl alcohol, e.g. as known and commercially available under the trade name HD Eutanol® from e.g. Henkel, Germany, may be used;
iii) fatty acids, saturated and/or unsaturated, branched and/or unbranched, having e.g. a $C_8$ to $C_{24}$ chain, e.g. oleic acid and/or lauric acid; and
iv) fatty oils, comprising e.g. mono-, di- and tri-glycerides, having e.g. $C_8$ to $C_{24}$ fatty acids, e.g. a medium chain fatty acid triglyceride, e.g. Miglyol® 812. Miglyol® 812 is a fractionated coconut oil comprising caprylic-capric acid triglycerides and having a molecular weight of about 520 daltons. Fatty acid composition=$C_6$ max. about 3%, $C_8$ about 50 to 65%, $C_{10}$ about 30 to 45%, $C_{12}$ max 5%; acid value about 0.1; saponification value about 330 to 345; iodine value max 1. Miglyol® 812 is commercially available from e.g. Hüls Chemie AG, Germany.

The polar solvents may be selected from a group comprising
i) glycols, e.g. glycerol, propylene glycol, butylene glycol, hexylene glycol. Propylene glycol may be commercially available from e.g. Dow Chemical;
ii) alcohols, having e.g. a $C_1$ to $C_7$ chain, branched and/or unbranched, e.g. isopropanol;
iii) dimethyl isosorbide, e.g. as known and commercially available under the trade name Arlasolve® DMI from ICI, Germany; and
iv) propylene carbonate.

The liquid means to solubilize the ascomycin may consist of one component or a mixture of components. Preferably the liquid means may be isopropyl myristate. The liquid means may be present in amount of from 1 to 20%, preferably from 2 to 15%, more preferably about 5% by weight based on the total weight of the composition.

Preferably the composition is in the form of an ointment, containing no added water, e.g a water content of less than 5 or 2%.

The liquid means may serve to dissolve partially the active agent. Typically 1 to 5% of the active agent is dissolved. Preferably a saturated solution of the active agent in the composition is obtained.

Preferably the ascomycin and the liquid means are present in a weight ratio of 0.05 to 3:1 to 15, more preferably in a weight ratio of 0.1 to 2:2 to 10, even more preferably in a weight ratio of 0.4 to 1:about 5.

Preferably the ascomycin, the urea, the hydrocarbon and the liquid means, when present, are present in a weight ratio of 0.05 to 3:0.1 to 20:70 to 95:1 to 15, more preferably in a weight ratio of 0.1 to 2:5 to 15:75 to 90:2 to 10, even more preferably in a weight ratio of 0.4 to 1:about 5:about 85:about 5.

The components of the carrier vehicle may be described in Fiedler, H. P., loc. cit., the contents of which are hereby incorporated by reference.

The compositions of this invention may be water-free or substantially water-free. The compositions may however comprise water, e.g. in an amount of from 0 to about 10% by weight based on the total weight of the composition, e.g. from 0.5 to 5%, e.g. from 1 to 3%. Preferably the compositions of this invention may be water-free.

The compositions of the invention are preferably in the form of an ointment.

If desired, stabiliser agents to hinder degradation of urea may be included, e.g. allantoin, acteylglyceride, propionic acid ester, taurin, collagen, collagen hydrolysate, amino acid salts, monoalkyiphosphate diethanolamine, triacetin, lactic acid, polysaccharides, chelating agents, e.g. citric acid or EDTA, e.g. as described in Fiedler, H. P. (loc. cit., 1, page 737).

Further components, e.g. preserving agents, e.g. microorganism growth inhibitors, and antioxidants, such as benzyl alcohol, butyl-hydroxytoluene, ascorbyl palmitate, sodium pyrosulfite, butyl hydroxy anisole, propyl p-hydroxybenzoate, methyl p-hydroxybenzoate, sorbic acid, chlorcresol and tocopherol may be included as appropriate. Preserving agents and antioxidants are preferably present in an amount of about 0.01 to about 2.5% by weight based on the total weight of the composition.

If desired, pH modifying agents may be included to bring the pH of the composition to between 4 and 6 or by adding a pharmaceutically acceptable buffer system. A pH of between 4 and 6 is desirable to avoid skin irritation.

If desired, the compositions of the invention may further comprise thickeners, e.g. to stabilize the compositions, e.g.
  i) solid alcohols, having e.g. a $C_{12}$ to $C_{24}$ chain, e.g. cetyl alcohol and/or stearyl alcohol. Cetyl alcohol and stearyl alcohol may be commercially available e.g. under the trade names Lorol® C16 and Lorol® C18, respectively, from Henkel, Germany;
  ii) solid acids, having e.g. a $C_{12}$ to $C_{24}$ chain, e.g. stearic acid and its salts, e.g. aluminium- or magnesium stearate;
  iii) esters, e.g. solid esters, of glycerol, e.g. mono-, di-, or tri-esters, e.g. glycerol monostearate and/or hydrogenated castor oil. Glycerol monostearate may be commercially available under the trade name Atmul® 84K from ICI, Germany;
  iv) esters, e.g. solid esters, of propylene glycol, e.g. mono- or di-esters, e.g. propylene glycol monooleate;
  v) inorganic thickening agents, e.g. magnesium sulfate, bentonite or silicates including hydrophilic silicon dioxide products, e.g. alkylated, for example methylated, silica gels, in particular colloidal silicon dioxide products as known and commercially available under the trade name Aerosil, e.g. Arosil® 200, Aerosil® R812 or Aerosil® R 972, e.g. from Degussa, Germany (Handbook of Pharmaceutical Excipients, 2nd Edition, Editors A. Wade and P. J. Weller (1994), Joint publication of American Pharmaceutical Association, Washington, USA and The Pharmaceutical Press, London, England, page 424-427);
  vi) solid waxes, e.g. bees wax or carnauba wax; and
  vii) esterified compounds of fatty acid and fatty alcohols. They may include esterified compounds of fatty acid having e.g. a $C_{12}$ to $C_{24}$ chain, saturated or unsaturated, and primary alcohol having e.g. a $C_{12}$ to $C_{24}$ chain, e.g. cetyl palmitate.

Thickening agents are preferably present in an amount of from about 1% to about 30%, e.g. from about 2% to about 10%, by weight based on the total weight of the composition.

The compositions of the present invention may further comprise emulsifiers, e.g.
  i) Polyoxyethylene-sorbitan-fatty acid esters, for example mono- and tri-lauryl, palmityl, stearyl and oleyl esters of the type known and commercially available under the trade name Tween® (Fiedler, loc. cit. p. 1615 ff), including the products Tween®
    20 [polyoxyethylene(20)sorbitanmonolaurate],
    21 [polyoxyethylene(4)sorbitanmonolaurate],
    40 [polyoxyethylene(20)sorbitanmonopalmitate],
    40 [polyoxyethylene(20)sorbitanmonostearate],
    60 [polyoxyethylene(20)sorbitantristearate],
    80 [polyoxyethylene(20)sorbitanmonooleate],
    81 [polyoxyethylene(5)sorbitanmonooleate],
    85 [polyoxyethylene(20)sorbitantrioleate].
  Especially preferred products of this class are Tween® 60 and Tween® 65.
  ii) Sorbitan fatty acid esters, e.g. sorbitan mono $C_{12-18}$ fatty acid esters, or sorbitan tri $C_{12-18}$ fatty acid esters as known and commercially available under the trade mark Span® or Arlacel®. Particularly preferred are the products Arlacel® 83 (Sorbitan sesquioleate) available from ICI, Germany, or Span® 60 (Sorbitan monostearate) (Fiedler, loc. cit., 2, p. 1430; Handbook of Pharmaceutical Excipients, loc. cit., page 473).
  iii) Polyoxyethylene alkyl ethers, e.g. polyoxyethylene glycol ethers of $C_{12}$ to $C_{18}$ alcohols, e.g. Polyoxyl 2-, 10- or 20-cetyl ether or Polyoxyl 4- or 23-lauryl ether, or polyoxyl 2-, 10- or 20-oleyl ether, or Polyoxyl 2-, 10-, 20- or 100-stearyl ether, as known and commercially available under the trade name Brij® from e.g. ICI, Germany. An especially preferred product of this class is e.g. Brij® 30 (Polyoxyl 4 lauryl ether) or Brij® 72 (Polyoxyl 2 stearyl ether) (Fiedler, loc. cit., 1, pp. 259; Handbook of Pharmaceutical Excipients, loc. cit., page 367).
  iv) Polyoxyethylene fatty acid esters, for example polyoxyethylene stearic acid esters of the type known and commercially available under the trade name Myrj® (Fiedler, loc. cit., 2, p. 1042; Handbook of Pharmaceutical Excipients, loc. cit., page 379). An especially preferred product of this class is Myrj® 52 (Polyoxyethylene 40 stearate) having a $D^{25}$ of about 1.1., a melting point of about 40 to 44° C., an HLB value of about 16.9, an acid value of about 0 to 1 and a saponification no. of about 25 to 35.
  v) Sucrose fatty esters, e.g. sucrose fatty acid esters. The fatty acid moiety may comprise saturated or unsaturated fatty acids or mixtures thereof. Particularly suitable are $C_{6-18}$-fatty acid saccharide mono- or diesters, in particular water soluble $C_{6-18}$ fatty acid saccharide mono- or diesters. Especially suitable are caproic ($C_6$), caprylic ($C_8$), capric ($C_{10}$), lauric ($C_{12}$), myristic ($C_{14}$), palmitic ($C_{16}$), oleic ($C_{18}$), ricinoleic ($C_{18}$) and 12-hydroxystearic ($C_{18}$) acid saccharide mono- or diesters, e.g. sucrose distearate, e.g. as known and commercially available under the trade name Sucro Ester® 7 from Gattefossé, France.

vi) Silicone emulsifiers, e.g. laurylmethicone copolyol, e.g. as known and commercially available under the trade name Emulsifier® 10 from Dow Corning or a mixture of cetyldimethicone copolyol, polyglyceryl-4-isostearate and hexyl laurate, e.g. as known and commercially available under the trade name Abil® WE-09 from Goldschmidt.

vi) Phospholipids, in particular lecithins (Fiedler, H. P., "Lexikon der Hilfsstoffe für Pharmazie, Kosmetik and angrenzende Gebiete", Editio Cantor Verlag Aulendorf, Aulendorf, 4th revised and expanded edition (1996), vol 2, p. 910, 1184). Lecithins suitable for use in the compositions of the invention include egg lecithins or soybean lecithins, in particular soybean lecithins, e.g. as known and commercially available under the trade name Phospholipon® 80 from Rhone Poulenc Rorer. Phospholipon® 80 is a phospholipid fraction with about 76% phosphatidylcholine, about 8% phosphatidic acid, about 4% phosphatidyl ethanolamine, and about 9% other lipids (manufacturer information).

vii) Lanolin, e.g. anhydrous lanolin (Fiedler, H. P., loc. cit., 2, p. 896).

It is to be appreciated that emulsifiers may be complex mixtures containing side products or unreacted starting products involved in the preparation thereof, e.g. emulsifiers made by polyoxyethylation may contain another side product, e.g. polyethylene glycol.

Compositions additionally comprising emulsifiers may be particularly suitable if it is desirable to easily wash them off the skin.

The compositions of the invention may further include, e.g. perfumes and/or coloring agents, as appropriate.

The compositions according to the invention are useful in the treatment of subacute and chronic inflammatory and hyperproliferative skin diseases and of cutaneous manifestations of immunologically-mediated diseases. Examples of such diseases are psoriasis, atopic dermatitis, contact dermatitis and further eczematous dermatitises, seborrhoic dermatitis, Lichen planus, a lichenified form of atopic dermatitis, vitiligo, Pemphigus, bullous Pemphigoid, Epidermolysis bullosa, urticaria, angioedemas, vasculitides, erythemas, cutaneous eosinophilias, Lupus erythematous and Alopecia areata.

In another aspect the present invention provides a composition as defined above for use in the treatment of inflammatory and hyperproliferative skin diseases and of cutaneous manifestations of immunologically-mediated diseases.

In another aspect the present invention provides a method for treating inflammatory and hyperproliferative skin diseases and of cutaneous manifestations of immunologically-mediated diseases comprising administering a composition as defined above to the skin of a patient in need thereof.

In another aspect the present invention provides the use of a composition as defined above in the preparation of a medicament for administering to the skin of a patient in need thereof.

In yet another aspect the present invention provides the use of a composition as defined above in the preparation of a medicament for the treatment of inflammatory and hyperproliferative skin diseases and of cutaneous manifestations of immunologically-mediated diseases.

In yet another aspect the present invention, provides the use of a carrier vehicle as defined above to enhance penetration of an ascomycin through human skin.

The carrier vehicle may be in the form of an ointment.

The compositions of the invention may be prepared in a conventional manner by working up the components into a pharmaceutical composition.

For example, the composition of the invention may be obtained by suspending the ascomycin and the urea in a mixture of liquid hydrocarbons and the lipophilic or polar solvent. Solid hydrocarbons may be mixed into the suspension in conventional manner. Alternatively, the composition of the invention may be obtained by suspending the ascomycin and the urea in a mixture of liquid hydrocarbons, solid hydrocarbons and the solvent as conventional. Other, e.g conventional, excipients may be added at the appropriate time.

The utility of the compositions according to the invention can be observed in standard clinical tests such as the test set out below.

A representative clinical trial is carried out as follows:

A randomised double-blind, vehicle-controlled within-patient study comparing a composition of the invention at a dose of 0.1 to 2% by weight (based on the total weight of the composition) active agent over e.g. 10 cm$^2$, corresponding to a dose of about 0.1 to 1 mg/cm$^2$, and if desired 0.005% calcipotriol ointment and/or 0.05% clobetasol-17-propionate ointment as positive control is performed in patients with chronic plaque type psoriasis.

In total 16 to 26 patients are treated with the composition twice daily for three weeks. The therapeutic effect on erythema, induration and scaling is evaluated for each of three clinical signs. In addition, the time to partial clearance is used for efficacy. Local tolerability of study medications and routine safety parameters, including haematology and clinical chemistry, are recorded.

The compositions of the invention are found to be effective without occlusion by technical means, e.g. the Finn chamber technique, e.g. under open application conditions.

The exact amount of the ascomycin and of the composition to be administered depends on several factors, for example the desired duration of treatment and the rate of release of the ascomycin. Satisfactory results are obtained in larger mammals, e.g. humans, with the local application over the area to be treated of a 0.1 to 2% by weight, preferably 1% by weight, concentration of the ascomycin once or several times a day (for example 2 to 5 times a day). In general the compositions may be applied to areas of skin as small as 1 cm$^2$ to as large as 1 m$^2$. Suitable skin loadings of the ascomycins fall within the range of from 0.001 mg/cm$^2$ to about 3 mg/cm$^2$, e.g. of from 0.1 mg/cm$^2$ to about 1 mg/cm$^2$.

In particular the utility of the compositions according to the invention can be observed in standard clinical tests such as the test set out in Example 1 infra using a concentration of 0.1 to 2% by weight (based on the total weight of the composition) active agent. The formulation of Example 1 was found to be effective in psoriasis.

The compositions of this invention are well tolerated on skin. Good skin penetration and permeation rates may be achieved using the compositions of the invention.

The compositions of this invention have the advantage of few components, are straightforward to prepare and are well-tolerated on human skin.

The following Examples illustrate the invention.

EXAMPLE 1.1

An ointment is prepared having the following composition (amounts in g)

| | |
|---|---|
| Compound A | 1 |
| Urea | 10 |
| Petrolatum | 39 |
| Wax, microcrystalline | 10 |
| Paraffin, liquid | 35 |
| Isopropyl myristate | 5 |
| Total | 100 |

The composition is prepared by suspending Compound A and urea in liquid paraffin and isopropylmyristate and heating to about 70° C. White petrolatum and microcrystalline wax are heated to about 85° C., cooled to about 70° C. and slowly added to the ascomycin mixture. The composition is then cooled to room temperature. An ointment is formed.

In total 20 patients were treated for three weeks. The therapeutic effect on erythema, induration and scaling was evaluated for each of three clinical signs. In addition, the time to partial clearance was used for efficacy. Local tolerability of study medications and routine safety parameters, including haematology and clinical chemistry, were recorded.

The formulation of Example 1 was effective. Local tolerability of the study medications tested was good and no systemic side effects were observed.

EXAMPLE 1.2

An ointment is prepared having the same composition as in Example 1.1.

The composition is prepared by heating liquid paraffin, microcrystalline wax, white petrolatum and isopropylmyristate to about 85° C., cooling to about 70° C. and suspending Compound A and urea in the mixture obtained. The composition is then cooled to room temperature. An ointment is formed.

| Example | 2 | 3 | 4 | 5 | 6 | 7 |
|---|---|---|---|---|---|---|
| Compound A | 1 | 0.1 | 1 | 2 | 2 | 1.5 |
| Means to retain water in the outer skin layer | | | | | | |
| Urea | 5 | 0.1 | 10 | 7.5 | 10 | 2 |
| Means to hinder water evaporating from the skin | | | | | | |
| Petrolatum | 44 | 99.8 | 84 | 85.5 | 86 | 73 |
| Wax, microcryst. | 10 | — | — | — | — | — |
| Paraffin, liquid | 35 | — | — | — | — | 20 |
| Liquid means | | | | | | |
| Isopropyl myristate | 5 | — | — | — | — | — |
| Diisopropyl adipate | — | — | 5 | — | — | — |
| Oleyl erucate | — | — | — | — | — | 3.5 |
| Oleyl alcohol | — | — | — | 5 | — | — |
| Propylene glycol | — | — | — | — | 2 | — |
| Total | 100 | 100 | 100 | 100 | 100 | 100 |

| Example | 8 | 9 | 10 | 11 | 12 | 13 |
|---|---|---|---|---|---|---|
| Compound A | 1 | 1 | 0.2 | 0.5 | 0.5 | 1 |
| Means to retain water in the outer skin layer | | | | | | |
| Urea | — | — | — | 10 | 3 | 10 |
| Sodium lactate | 5 | — | — | — | — | — |
| Sodium chloride | — | 15 | — | — | 3 | — |
| Sodium 2-pyrrolidone-5-carboxylate | — | — | 2 | — | — | — |
| Means to hinder water evaporating from the skin | | | | | | |
| Petrolatum | 69 | — | 75.8 | 61.5 | 87.5 | 87 |
| Wax, microcryst. | — | — | 5 | 2 | — | — |
| Paraffin, liquid | 15 | — | 15 | — | — | — |
| Plastibase ® | — | 84 | — | — | — | — |
| Liquid means | | | | | | |
| Oleyl oleate | — | — | — | — | — | 7 |
| Oleyl alcohol | — | — | — | 10 | — | — |
| Miglyol ® 812 | — | — | 2 | — | — | — |
| Propylene glycol | — | — | — | 5 | — | — |
| Dimethyl isosorbide | — | — | — | — | 2 | — |
| Thickeners | | | | | | |
| Cetyl alcohol | 5 | — | — | — | — | — |
| Stearyl alcohol | 5 | — | — | — | — | — |
| Glycerol monostearate | — | — | — | — | 5 | — |
| Aerosil ® 200 | — | — | — | 4 | — | — |
| Emulsifiers | | | | | | |
| Sorbitan sesquioleate | — | — | — | — | 5 | 5 |
| Water | — | — | — | 2 | — | — |
| Total | 100 | 100 | 100 | 100 | 100 | 100 |

Compound A in the compositions described in Example 1 to 13 may be replaced by Compound B, C, D, E, or F or FK 506.

Compounds A, B, C, D, E or F or FK 506 may be used in micronized or non micronized form.

Urea may be used in micronized or non micronized form.

Examples 2 to 13 may be prepared according to Example 1.1 or 1.2.

The invention claimed is:

1. A composition for topical administration for treatment of skin disorders which composition comprises: 33-epi-chloro-33-desoxy-ascomycin and a carrier vehicle comprising
    (i) a moisturizer consisting of a urea, an inorganic salt, and a carboxylic acid or a derivative thereof selected from the group consisting of glycolic acid, 2-pyrrolidone-5-carboxylate, salts thereof, and mixtures thereof;
    (ii) a component to hinder water evaporating from the skin consisting of at least one hydrocarbon; and
    (iii) a solvent selected from the group consisting of a lipophilic solvent, a polar solvent, and mixtures thereof;
    wherein 33-epi-chloro-33-desoxy-ascomycin is present in an amount of 0.1 to 2% by weight;
    wherein the moisturizer is present in an amount of 5 to 15%;
    wherein the at least one hydrocarbon is present in an amount of 75 to 90%;
    wherein the solvent is present in an amount of 2 to 10%; and
    wherein the composition is substantially water-free.

2. A composition as claimed in claim 1 wherein the hydrocarbon is selected from the group consisting of petrolatum, liquid paraffin, microcrystalline wax, solid paraffin, and a reaction product of paraffin and polyethylene.

3. A composition as claimed in claim 1 wherein the solvent comprises a wax, a fatty alcohol, a fatty acid, or a fatty oil.

4. A composition as claimed in claim 3 wherein the solvent is isopropyl myristate.

5. A method of enhancing penetration of an ascomycin through human skin, comprising applying to skin of a patient in need thereof a therapeutically effective amount of the composition of claim 1.

6. A method of treating inflammatory and hyperproliferative skin diseases and cutaneous manifestations of immunologically-mediated diseases, comprising applying to skin of a patient in need thereof a therapeutically effective amount of the composition of claim 1.

7. A composition as claimed in claim 1 wherein the composition is water-free.

* * * * *